(12) United States Patent
Galea et al.

(10) Patent No.: US 8,953,154 B2
(45) Date of Patent: Feb. 10, 2015

(54) ORIENTATION TRACKING SYSTEM AND METHOD

(75) Inventors: Anna M Galea, Stow, MA (US);
Kristen J. LeRoy, Somerville, MA (US); Gordon Hirschman, Cohoes, NY (US)

(73) Assignee: Vivonics, Inc., Waltham, MA (US)

( * ) Notice: Subject to any disclaimer, the term of this patent is extended or adjusted under 35 U.S.C. 154(b) by 323 days.

(21) Appl. No.: 13/558,736

(22) Filed: Jul. 26, 2012

(65) Prior Publication Data

US 2014/0031723 A1    Jan. 30, 2014

(51) Int. Cl.
*G01B 11/26*    (2006.01)

(52) U.S. Cl.
USPC ........................................................ 356/138

(58) Field of Classification Search
CPC ...................................................... G01B 11/26
USPC ............................................. 356/138; 33/367
See application file for complete search history.

(56) References Cited

U.S. PATENT DOCUMENTS

| | | | | |
|---|---|---|---|---|
| 3,984,918 | A * | 10/1976 | Chaney | 33/366.18 |
| 4,503,622 | A * | 3/1985 | Swartz et al. | 33/366.14 |
| 4,549,078 | A * | 10/1985 | Monahan | 250/203.1 |
| 4,561,081 | A * | 12/1985 | Janssen et al. | 369/44.17 |
| 4,587,741 | A | 5/1986 | Rorden et al. | |
| 4,606,133 | A * | 8/1986 | Mills | 33/366.14 |
| 5,335,190 | A | 8/1994 | Nagle et al. | |
| 5,645,077 | A | 7/1997 | Foxlin | |
| 5,807,284 | A | 9/1998 | Foxlin | |
| 6,162,191 | A | 12/2000 | Foxlin | |
| 6,529,331 | B2 * | 3/2003 | Massof et al. | 359/630 |
| 6,786,877 | B2 | 9/2004 | Foxlin | |
| 7,301,648 | B2 * | 11/2007 | Foxlin | 356/620 |
| 2002/0162235 | A1 * | 11/2002 | Rando | 33/366.16 |
| 2003/0158699 | A1 * | 8/2003 | Townsend et al. | 702/151 |
| 2010/0266171 | A1 * | 10/2010 | Wendler et al. | 382/128 |

FOREIGN PATENT DOCUMENTS

| | | | | |
|---|---|---|---|---|
| EP | 2594197 | * | 5/2013 | A61B 5/06 |
| WO | WO2013/076163 | * | 5/2013 | A61B 5/06 |

OTHER PUBLICATIONS

Berger et al., "Hearing protection: Surpassing the limits to attenuation imposed by the bone-conduction pathways", J. Acoust. Soc. Am. 114(4), Pt. 1, Oct. 2003, pp. 1955-1967.

* cited by examiner

*Primary Examiner* — Roy M Punnoose
(74) *Attorney, Agent, or Firm* — Iandiorio Teska & Coleman, LLP (57) ABSTRACT

An orientation tracking system including a first tracking system subject to drift. A second tracking system is configured to provide an output for calibrating the first tracking system to reduce the drift of the first tracking system. The second tracking system includes at least one inclinometer, each inclinometer including a light source adjacent one side of the inclinometer, a light sensor adjacent an opposing side of the inclinometer, and a light obscuring material within the inclinometer for obscuring the light between the light source and light sensor to indicate an orientation of the inclinometer.

23 Claims, 6 Drawing Sheets

ORIENTATION TRACKING SYSTEM AND METHOD

GOVERNMENT RIGHTS

This invention was made with U.S. Government support under Contract No. FA8650-07-M-6778 and Contract No. FA8650-08-C-6840 awarded by the U.S. Air Force. The Government has certain rights in the invention.

FIELD OF THE INVENTION

This subject invention relates to a system and method for tracking the orientation of a person or an object.

BACKGROUND OF THE INVENTION

Orientation tracking systems are used to track the position and orientation of a person, a part of a person, e.g., the head, or an object. A few conventional uses of orientation tracking systems include flight simulators and immersive training simulators, such as medical driving simulators.

One key orientation tracking system is a head orientation tracking system for flight deck personnel. These systems typically track the position and orientation of a subject on the flight deck of an aircraft carrier or airfield. This may be of considerable importance when a clear line of sight of the person or clear GPS link cannot be assured. The head orientation tracking system may also be used to return directional sound queues to the flight deck personnel to orient them when hearing protection is being used. For example, a head orientation tracking system may provide sound queues regarding incoming flights at a time when flight deck personnel may not be able to hear them due to the hearing protection needed for the high sound levels.

Conventional head orientation tracking systems may not be appropriate for use on a flight deck. For example, one conventional head tracking system relies on using magnets which may not operate adequately in the very high electromagnetic environment of a flight deck. Other conventional head orientation tracking system relies on ultrasonic or IR technologies. Such a system may require a direct line of sight. Video tracking head orientation tracking systems are also not desirable because they can be bulky and operate slowly. Other conventional head orientation tracking system may rely on the use of an inertial mass MEMS sensor. Such a system may be subject to stochastic noise that, when integrated twice to determine position, may create considerable drift which over time will provide an inaccurate reading of location.

Inclinometers, which can be used to determine orientation in one direction, are relatively known in the art. Liquid with a gas bubble is used in standard inclinometers such as levels found at most hardware stores. U.S. Pat. No. 4,587,741 discloses an inclinometer having a toroidal race containing a spherical ball free to move therein under the influence of gravity. Multiple such inclinometers can also be implemented in a system. However, the inclinometer disclosed in the '741 patent uses electrodes to sense the position of the ball. Such an inclinometer may not work adequately in environments which are exposed to high electromagnetic fields. U.S. Pat. Nos. 5,645,077, 5,807,284, 6,162,191, and 6,786,877 B2 each disclose an inertial orientation tracker with automatic drift compensation. Each of these systems, however, is large and relies on a mechanical design.

BRIEF SUMMARY OF THE INVENTION

In one aspect, an orientation tracking system is featured including a first tracking system subject to drift. A second tracking system is configured to provide an output for calibrating the first tracking system to reduce the drift of the first tracking system. The second tracking system includes at least one inclinometer, each inclinometer including a light source adjacent one side of the inclinometer, a light sensor adjacent an opposing side of the inclinometer, and a light obscuring material within the inclinometer for obscuring the light between the light source and light sensor to indicate an orientation of the inclinometer.

In one example, each inclinometer may include a hollow toroid having the light obscuring material therein. The second tracking system may include three inclinometers oriented orthogonally to with respect to each other. The light obscuring material may be a solid ball. Each inclinometer may also include a fluid therein for stabilizing the ball. The light obscuring material may include a light absorbing fluid. The fluid may include ink. Each inclinometer may also include a second fluid having a lower viscosity than the liquid absorbing fluid. Each inclinometer may further include a gas. The light source may include a light emitting diode (LED). The light sensor may include a photodiode or a phototransistor.

In another aspect, an orientation tracking system is featured including a first tracking system subject to drift. A second tracking system is configured to provide an output for calibrating the first tracking system to reduce the drift of the first tracking system. The second tracking system includes at least three inclinometers, each inclinometer including a hollow circular tube, a light source adjacent the tube on one of the inside or the outside of the circular tube, a light sensor adjacent the tube on the other of the inside or the outside of the circular tube, and a light obscuring material within the tube for obscuring the light between the light and light sensor to indicate an orientation of each tube.

In one example the three inclinometers may be oriented orthogonally to each other.

In another aspect, a head orientation tracking system is featured including a head mountable apparatus. A first tracking system is within the apparatus and is subject to drift. A second tracking system is within the apparatus. The second tracking system is configured to provide an output for calibrating the first tracking system to reduce the drift of the first tracking system. The second tracking system includes at least three inclinometers, each inclinometer including a hollow circular tube, a light source adjacent the tube on one of the inside or the outside of the circular tube, a light sensor adjacent the tube on the other of the inside or the outside of the circular tube, and a light obscuring material within the tube for obscuring the light between the light source and light sensor to indicate an orientation of each tube, the output of the second tracking system used to calibrate the first system to reduce drift thereof.

In one embodiment there may be three inclinometers oriented orthogonally with respect to each other. The circular tube may include a hollow toroid which includes the light obscuring material within the toroid.

In another aspect, an inclinometer system is featured including at least one inclinometer, each including a hollow circular tube, a light source adjacent the tube on one of the inside or the outside of the circular tube, a light sensor adjacent the tube on the other of the inside or the outside of the circular tube, and a light obscuring material within the tube for obscuring the light between the light source and light sensor to indicate an orientation of each tube.

In one design, the system may include three inclinometers oriented orthogonally to each other. The circular tube may include a hollow toroid which includes the light obscuring material within the toroid.

In another aspect, a method for orientation tracking is featured, the method includes the steps of: providing a first tracking system subject to drift, and providing a second tracking system in communication with the first tracking system which calibrates the first tracking system to reduce the drift of the first tracking system.

In one example, the first tracking system may be configured to calculate roll, pitch, and yaw of a person or object. The second tracking system may be configured to calculate a calibration factor. The method may include the step of adding the roll, pitch, and yaw with the calibration factor to determine if the second tracking system is positioned more accurate than the first tracking system.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
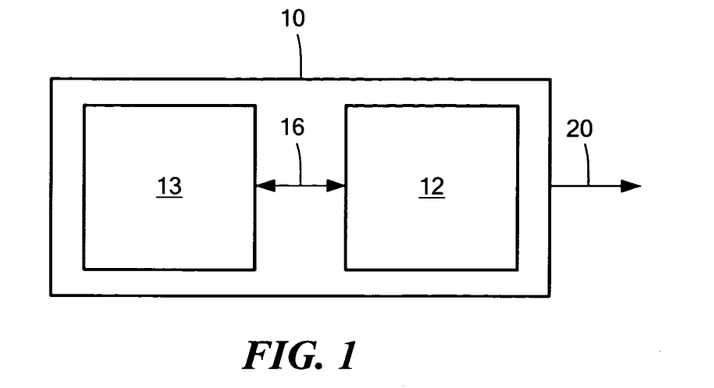
FIG. 1 is a block diagram of one embodiment of the orientation tracking system in accordance with the invention.

There is shown in FIG. 1 one embodiment orientation tracking system 10 of this invention. Orientation tracking system 10 includes first tracking system 12 which tracks a person or an object that may be subject to drift over time. The drift may cause the output of first tracking system 12 to become inaccurate. System 10 also includes a second tracking system 13 which communicates to first tracking system by line 16 to provide an output for calibrating first tracking system 12 to reduce its drift.

Figure 2A:
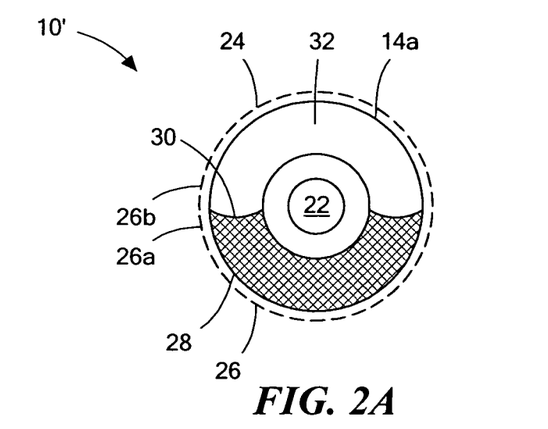
FIGS. 2A-2C are schematic diagrams of examples of inclinometers that may be used with the orientation tracking system shown in FIG. 1.
Figure 2B:
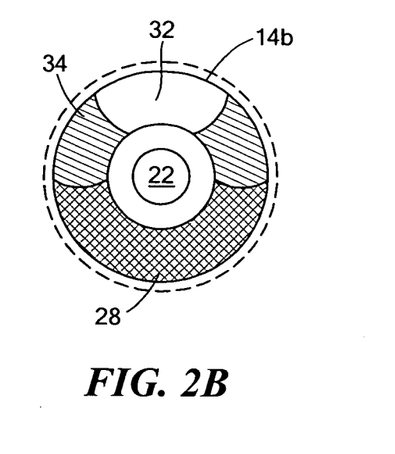
Figure 2C:
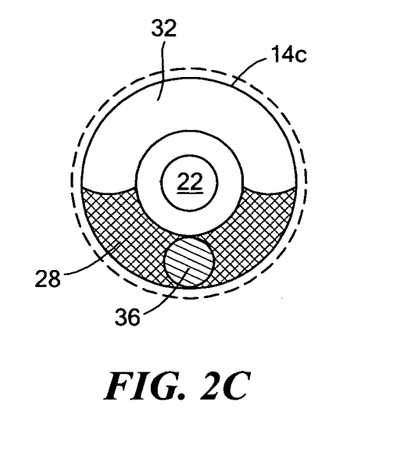

In one design, second tracking system 13 includes at least one inclinometer. The inclinometer may have various designs, e.g., as shown in FIGS. 2A-2C, where like parts have been given like numbers. For example, inclinometer 14a, FIG. 2A, includes light source 22, such as an LED or similar type light source, adjacent to one side of inclinometer 14a. Inclinometer 14a also preferably includes one or more light sensors 26, e.g., a photodiode(s), a photo-resistor(s), or similar type device located adjacent an opposing side of the inclinometer as shown. Light obscuring material 28, such as opaque ink or similar type material, is preferably located within inclinometer 14a to obscure the light between light source 22 and light sensor 26 to indicate an orientation of inclinometer 14a. In one example, light sensor 26 may include a plurality light sensors along the outer periphery of inclinometer 14a as shown which preferably determine the special location of light obscuring material 28 in inclinometer 14a. For example, light obscuring material 28 would obscure the light between light source 22 and light sensor 26a, but would not obscure the light between light sensor 22 and sensor 26b. This allows second tracking system 13, FIG. 1, to determine meniscus 30, FIG. 2A, created by light obscuring material 28 located between sensors 26a and 26b.

Inclinometer 14a is preferably a hollow toroid which includes light obscuring material 28 within the toroid. Inclinometer 14a may include a liquid and a gas, e.g., first liquid 28 and gas 32. In other example, inclinometer 14b, FIG. 2B, may include one or more liquids and a gas, e.g., first liquid 28, gas 32, and second liquid 34 as shown. In one design, inclinometer 14c, FIG. 2C, may include one or more liquids, a gas, and a solid, e.g., first liquid 28, gas 32, and solid ball 36.

Second tracking system 13, FIGS. 1-2C, preferably detects the location of light obscuring material 28 using low power consumption optical sensors, such as photologic optical switches, e.g., a model OPD 480 (DigiKey, Thief River Falls, Minn.). First tracking system 12, FIG. 1, may include an inertial mass sensor, such as model ADXRS300 (Analog Devices, Norwood, Mass.). In this design, the inertial mass sensor is preferably a 300 deg/sec angular rate sensor on a single chip or better. This sensor, like typical MEMS sensors, is subject to stochastic noise that, when integrated twice to determine position, results in considerable drift. To minimize the effect of this drift, the MEMS sensor may be placed in series with a low-pass filter and average its readings with the information provided by second tracking system 13.

Preferably, each inclinometer of second tracking system 13 as discussed above to one or more of FIGS. 2A-2C may be placed at an angle to the direction of interest, such as the Z axis. If light sensor 26 is placed perpendicular to the axis of interest, light obscuring material 28 may settle across the entire hoop of the inclinometer. By placing the inclinometer askew, in the absence of rotational motion, the light obscuring material 28 is biased to one location. With motion, however, the light obscuring material 28 will swivel about this bias point. This quaver in the light obscuring material 28 position may be combined with the data from the MEMS sensor to further filter the output of the MEMS sensor.

Figure 3:
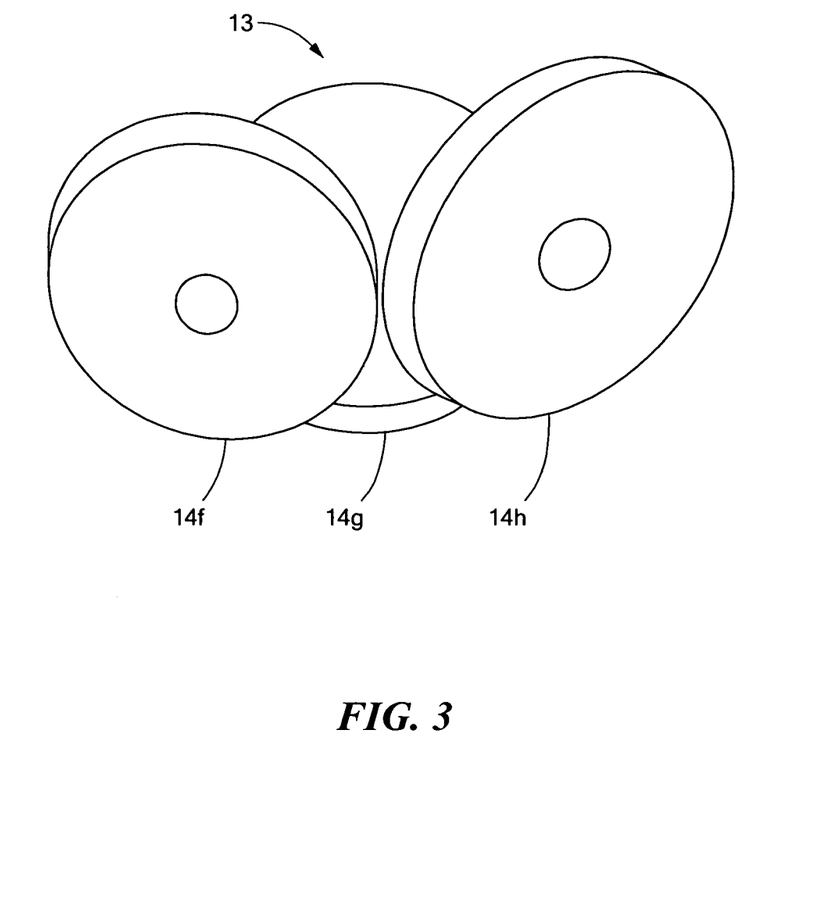
FIG. 3 is a schematic diagram of one example of the second tracking system shown in FIGS. 1-2C that includes three inclinometers arranged orthogonal to each other.

Preferably, second tracking system 13, FIGS. 1-2C includes three inclinometers, e.g., inclinometers 14f, 14g, and 14h, FIG. 3, to provide orientation information in three directions, to provide the roll, pitch, and yaw. Inclinometers 14f-14g may be mounted orthogonally with respect to each other as shown so that the roll, pitch, and yaw can be determined. When inclinometers 14f-14g are orientated orthogonally to each other, they may be turned in any direction, yet still cover these three axes of direction. Inclinometers 14f-14g may have other orientations rather than being orthogonal with respect to each other and still provide the same degree of coverage.

Preferably, light sensor 26, FIGS. 2A-2C, of second tracking system 13 includes a plurality of photodetectors, e.g., photodiodes. Typically, each photodiode will receive full light from light source 26, e.g., a light emitting diode (LED). This preferably causes each photodiode to act as a closed switch, which pulls the readout level shown in plot 40, FIG. 4A up to the battery voltage, e.g., indicated at 42, providing the maximum signal that can be received. When light obscuring material 28, FIGS. 2A-2C, e.g., a ball, opaque ink, or similar type light obscuring material, starts to obscure the field of view of a photodiode, the current provided by power supply 45, FIG. 4B, that passes through the photodiode decreases, thus weakening the signal level, e.g., indicated at 44, FIG. 4A, until all direct light is obscured. Note that due to refraction, it is not expected that the light obstructing material will completely obstruct light between the light source and the photodiode. Preferably, the signal levels should indicate when light is obscured the most. The signal level will typically increase again as the ball or light obstructing material moves away from the photodiode.

Figure 4A:
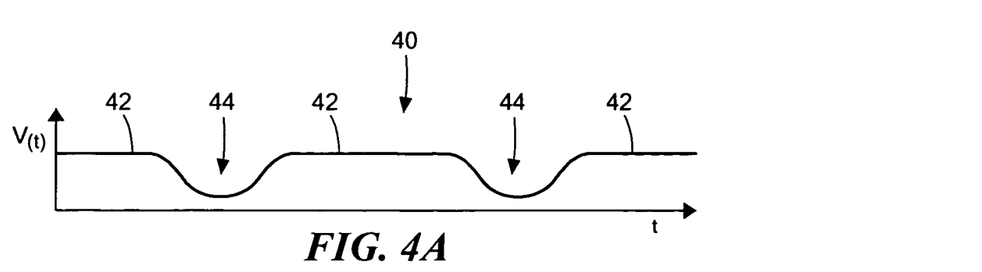
FIG. 4A is a plot showing one example of the voltage of a single photodiode signal versus time for the second tracking system that includes one or more of the inclinometers shown in FIGS. 2A-3.
Figure 4B:
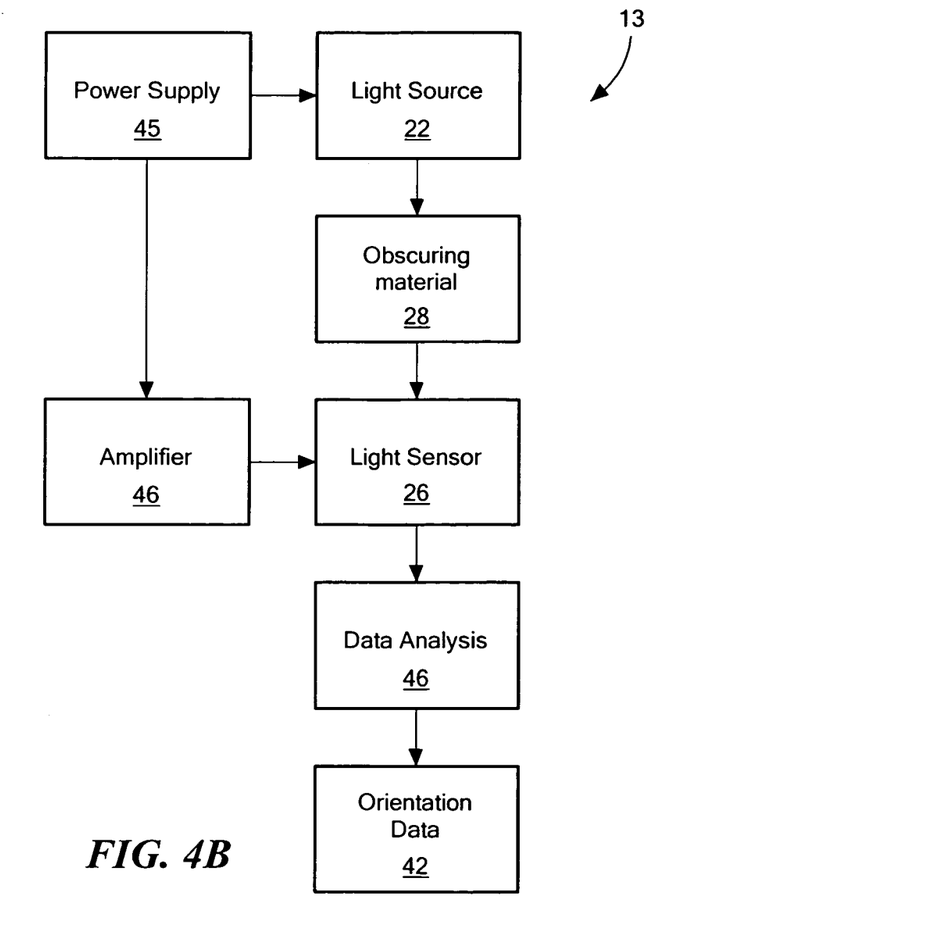
FIG. 4B is a schematic block diagram showing primary components of one embodiment of the second tracking system of this invention.

High input impedance inverting amplifier, 46, FIG. 4B, stage may be used to buffer each photodiode so that the waveform 40 shown in FIG. 4A will be inverted. High impedance amplifier 46 preferably limits the current that flows through each photodiode in the "on" illuminated state which helps to minimize power consumption in the photodiode.

Whether or not a high impedance amplifier is used to invert the polarity of each photodiode, the point at which a ball or light obscuring material is directly over the photodiode can be found as the peaks of the second derivative, since they will correspond to the points of highest concavity in the signal level. Being able to discern when the ball or light obscuring material 28 is directly over each photodiode, however, may result in less resolution due to the arc angles suspended by each photodiode. A better resolution may be achieved by using the information pertaining to the rise and fall of the signal levels.

Although as discussed above with reference to FIGS. 1-4B, the at least one inclinometer is shown as part of second tracking system 13, this is not a necessary limitation of this invention. In other embodiments, orientation tracking system 10', FIGS. 2A-2C, may include only one or more inclinometers 14a, 14b, 14c to indicate the orientation of the inclinometer in similar manner as discussed above. In one example, three inclinometers may be oriented orthogonally to each other to provide a three-dimensional inclinometer system.

Figure 5A:
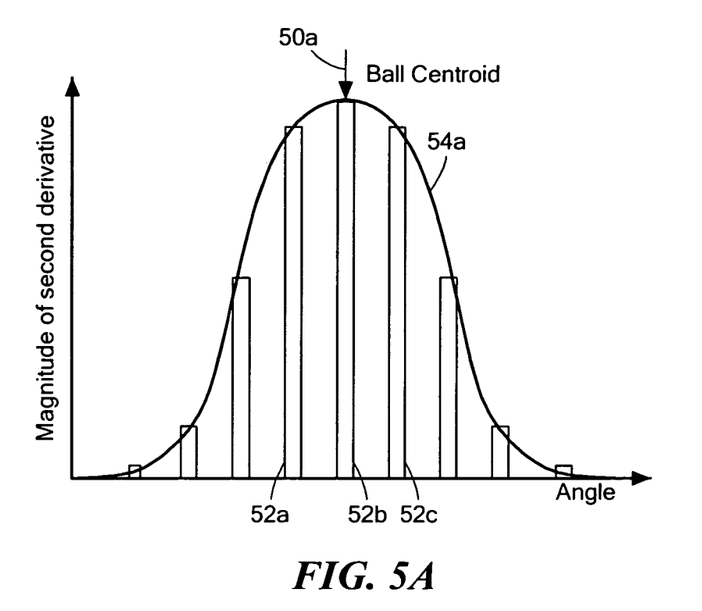
FIGS. 5A and 5B are graphs showing the magnitudes of the second derivatives of each photodiode for the second tracking system including one or more of the inclinometers shown in FIGS. 2A and 2B, respectively.
Figure 5B:
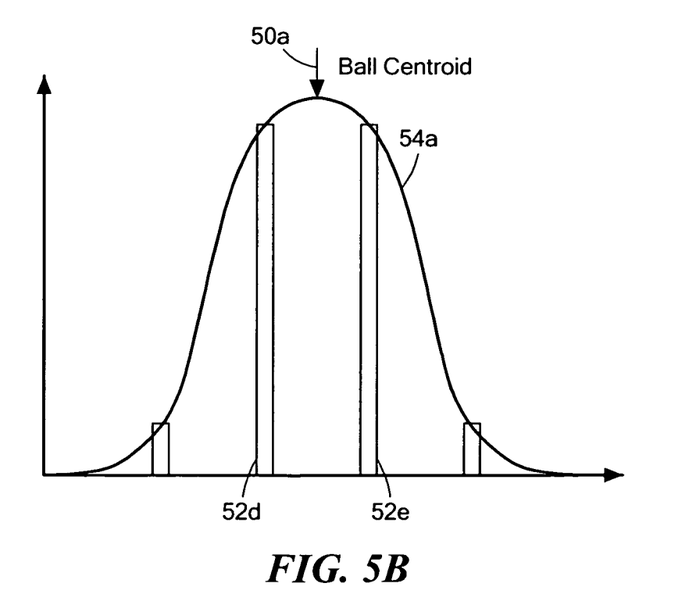

One example of an algorithm utilized by one embodiment of orientation tracking system 10 of this invention that exploits the relative measures of the photodiodes while remaining resistant to drift and changes in calibration is as follows. First, the second derivative of the photodiode signal levels are calculated by data analysis 46, FIG. 4B. This is because the second derivative is not susceptible to drift because all DC and linear drift components are eliminated. Second, centroid 50a, FIG. 5A and centroid 50b, FIG. 5B, of light obscuring material 28 can be found at the magnitude-weighted average location of the second derivatives 52a, 52b, 52c, FIG. 5A, and 52d, 52e, FIG. 5B. The relative magnitudes of second derivatives 52a-52c and 52d-52e will approximate a Gaussian curve as shown by lines 54a and 54b. The centroid 50a and 50b of the ball is at the centroid of curve 54a and 54b. When the arc angle that each photodiode subtends is much smaller than that of the ball, more samples will be available for calculating the second derivatives as can be seen by comparing FIGS. 5A and 5B. FIG. 5B shows second derivative for an inclinometer in which just over 3 photodiodes fit within the shadow of the ball. The results of data analysis 46 by second tracking system 13 are output as orientation data 47 which is used to calibrate first tracking system 12, FIG. 1. FIG. 4B is a schematic block diagram showing primary components of one embodiment of second tracking system 13 of this invention.

Figure 6:
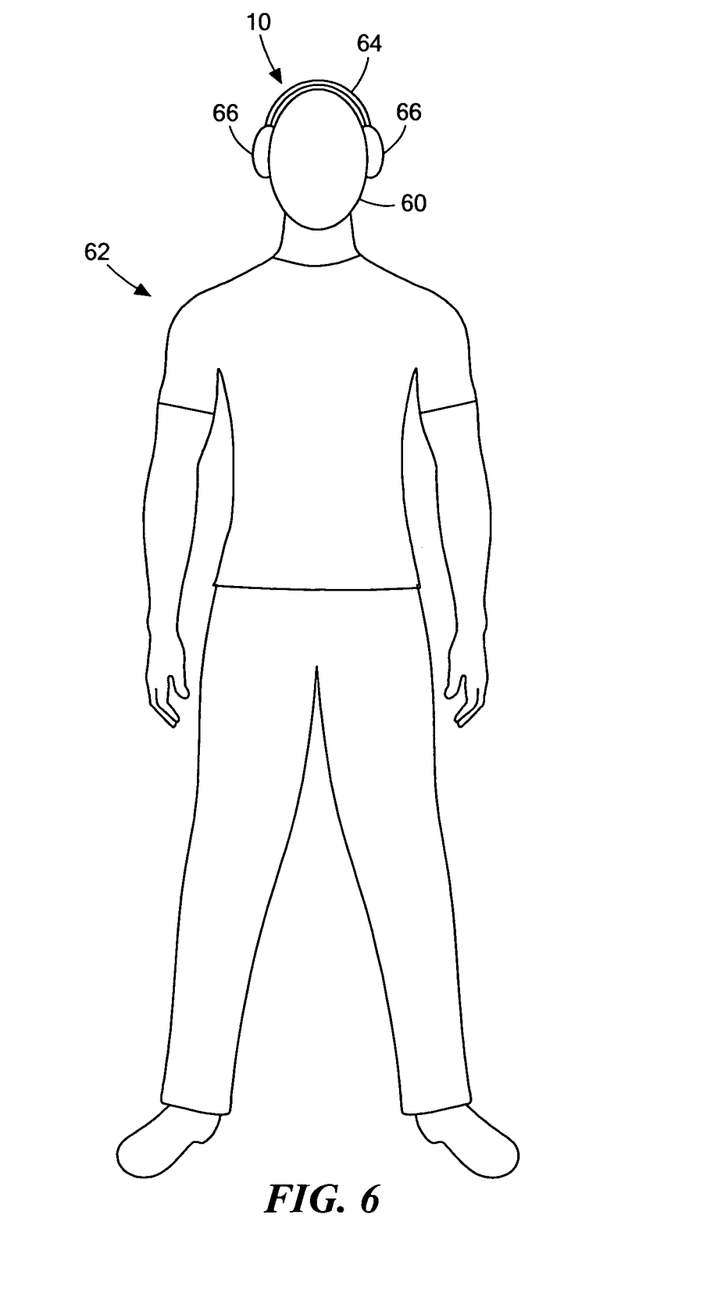
FIG. 6 is a schematic diagram of one example of a head orientation tracking system that incorporates the orientation system shown in one or more of FIGS. 1-3.

In one design, orientation tracking system 10 discussed above with reference to FIGS. 1-5B may be mountable on head 60, FIG. 6, of person or an object, e.g., person 62, to track the orientation of the person or object. In this example, orientation tracking system 10 includes head mountable apparatus 64 which preferably includes earphones 66 which may provide sound cues to the person. The sound cues may be advantageous if the person is wearing hearing protection such that they cannot otherwise discern the sounds around them without the sound cues being provided. Head mountable apparatus 64 may include a first tracking system 12, FIG. 1, subject to drift and a second tracking system 13 to calibrate the first tracking system to reduce its drift. Such a head orientation tracking system may be valuable for military applications, training applications in the medical and other fields, home entertainment gaming systems in which the system needs to know the exact location and/or orientation of the user and similar type applications.

One example of a method for using a second orientation system 13 to calibrate first calibration 12 is discussed below with reference to FIGS. 1-3 and FIG. 7.

Figure 7:
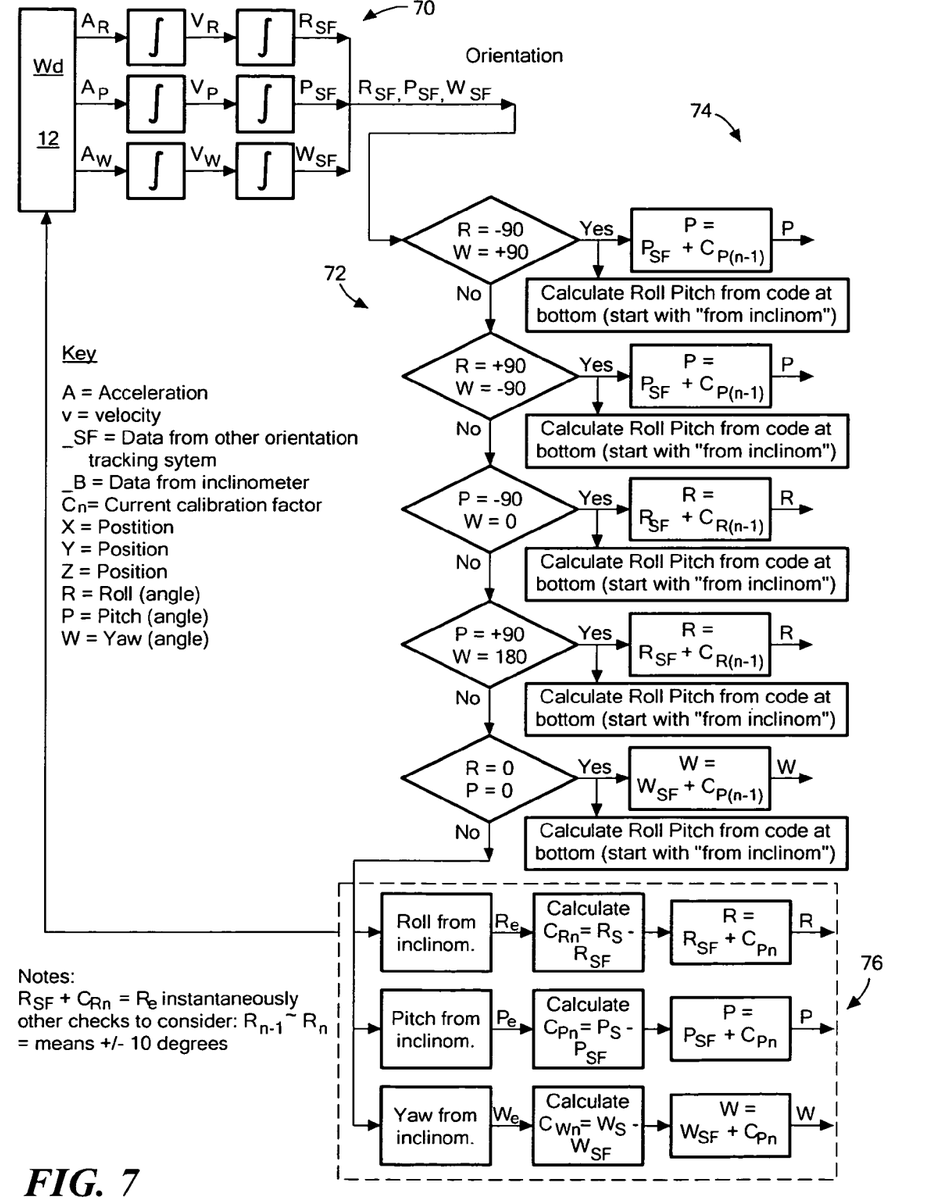
FIG. 7 is a flow chart for a method of calibrating the first orientation tracking system using the data from a second orientation tracking system in accordance with one embodiment of this invention.

In this example, first tracking system 12, FIG. 1, preferably outputs angular acceleration data for the roll, pitch, and yaw axes which is integrated once to obtain the angular velocity for the roll, pitch, and yaw axes, and then integrated again to obtain the roll, pitch, and yaw, RSF, PSF, WSF, indicated at 70, FIG. 7. As discussed above, these calculations may suffer from drift. To compensate for this drift, the actual roll, pitch, and yaw can be calculated by adding the roll, pitch, and yaw calculated from the first orientation tracking system 12 with a calibration factor calculated from second orientation tracking system 13, FIGS. 1-3. Orientation tracking system 10 first determines whether second orientation tracking system 13 is positioned to be more accurate than first orientation tracking system 12. This may be done with a logic tree. Five steps of one such exemplarily a tree are indicated at 72, FIG. 7. If second orientation system 13 is determined to be positioned to be more accurate in any or all of the three directions, then its values of pitch P, roll R, and/or yaw W are used, indicated at 74. If for any of these orientation directions this is not the case, a calibration factor calculated from the last instance of this is used.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed:

those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. An orientation tracking system comprising:
a first tracking system subject to drift;
a second tracking system configured to provide an output for calibrating the first tracking system to reduce the drift of the first tracking system, the second tracking system including at least one inclinometer, each inclinometer including:
a light source adjacent one side of the inclinometer;
a light sensor adjacent an opposing side of the inclinometer; and
a light obscuring material within the inclinometer for obscuring the light between the light source and light sensor to indicate an orientation of the inclinometer.

2. The system of claim 1 in which each inclinometer includes a hollow toroid having the light obscuring material therein.

3. The system of claim 1 in which the second tracking system includes three inclinometers oriented orthogonally to with respect to each other.

4. The system of claim 1 in which the light obscuring material is a solid ball.

5. The system of claim 4 in which each inclinometer also includes a fluid therein for stabilizing the ball.

6. The system of claim 1 in which the light obscuring material includes an opaque fluid.

7. The system of claim 6 in which the fluid includes a light absorbing fluid.

8. The system of claim 6 in which each inclinometer also includes a second fluid having a lower viscosity than the opaque fluid.

9. The system of claim 6 in which each inclinometer further includes a gas.

10. The system of claim 1 in which the light source includes a light emitting diode (LED).

11. The system of claim 1 in which the light sensor includes a photodiode.

12. The system of claim 1 in which the light sensor includes a phototransistor.

13. An orientation tracking system comprising:
a first tracking system subject to drift;
a second tracking system configured to provide an output for calibrating the first tracking system to reduce the drift of the first tracking system, the second tracking system including at least three inclinometers, each inclinometer including:
a hollow circular tube;
a light source adjacent the tube on one of the inside or the outside of the circular tube;
a light sensor adjacent the tube on the other of the inside or the outside of the circular tube; and
a light obscuring material within the tube for obscuring the light between the light and light sensor to indicate an orientation of each tube.

14. The system of claim 13 in which the three inclinometers are oriented orthogonally to each other.

15. A head orientation tracking system comprising:
a head mountable apparatus;
a first tracking system within the apparatus and subject to drift;
a second tracking system within the apparatus, the second tracking system configured to provide an output for calibrating the first tracking system to reduce the drift of the first tracking system, the second tracking system including at least three inclinometers, each inclinometer including:
a hollow circular tube;
a light source adjacent the tube on one of the inside or the outside of the circular tube;
a light sensor adjacent the tube on the other of the inside or the outside of the circular tube; and
a light obscuring material within the tube for obscuring the light between the light source and light sensor to indicate an orientation of each tube, the output of the second tracking system used to calibrate the first tracking system and reduce drift thereof.

16. The system of claim 15 in which there are three inclinometers oriented orthogonally with respect to each other.

17. The system of claim 15 in which the circular tube includes a hollow toroid which includes the light obscuring material within the toroid.

18. An inclinometer system comprising:
at least one inclinometer, each including:
a hollow circular tube including a hollow toroid which includes a light obscuring material within the toroid;
a light source adjacent the tube on one of the inside or the outside of the circular tube;
a light sensor adjacent the tube on the other of the inside or the outside of the circular tube; and
a light obscuring material within the tube for obscuring the light between the light source and light sensor to indicate an orientation of each tube.

19. The system of claim 18 in which the system includes three inclinometers oriented orthogonally to each other.

20. A method for orientation tracking, the method comprising the steps of:
providing a first tracking system subject to drift; and
providing a second tracking system including a hollow circular tube including a hollow toroid which includes a light obscuring material within the toroid, a light source adjacent the tube on one of the inside or the outside of the circular tube, a light sensor adjacent the tube on the other of the inside or the outside of the circular tube, the light obscuring material within the tube for obscuring the light between the light source and light sensor to indicate an orientation of each tube, the second tracking system in communication with the first tracking system which calibrates the first tracking system to reduce the drift of the first tracking system.

21. The method of claim 20 in which the first tracking system is configured to calculate roll, pitch, and yaw of a person or object.

22. The method of claim 20 in which the second tracking system is configured to calculate a calibration factor.

23. The method of claim 20 further including the step of adding the roll, pitch, and yaw with the calibration factor to determine if the second tracking system is positioned more accurate than the first tracking system.

* * * * *